United States Patent
Nishimura

(10) Patent No.: US 7,957,785 B2
(45) Date of Patent: Jun. 7, 2011

(54) WATERPROOF BIOELECTRODE

(75) Inventor: Naoki Nishimura, Kawaguchi (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 385 days.

(21) Appl. No.: 11/498,719

(22) Filed: Aug. 4, 2006

(65) Prior Publication Data
US 2007/0088227 A1 Apr. 19, 2007

(30) Foreign Application Priority Data
Aug. 9, 2005 (JP) .................................. 2005-231083

(51) Int. Cl.
*A61B 5/0408* (2006.01)
(52) U.S. Cl. ......... 600/391; 600/392; 600/393; 439/909
(58) Field of Classification Search ........... 600/391–393
See application file for complete search history.

(56) References Cited

U.S. PATENT DOCUMENTS

| | | | |
|---|---|---|---|
| 4,008,721 A | | 2/1977 | Burton |
| 4,102,331 A | * | 7/1978 | Grayzel et al. ............. 600/385 |
| 4,233,987 A | | 11/1980 | Feingold |
| 4,353,372 A | * | 10/1982 | Ayer ............................ 600/393 |
| 4,681,118 A | | 7/1987 | Asai et al. |
| 4,715,382 A | * | 12/1987 | Strand ......................... 600/392 |
| 4,763,660 A | * | 8/1988 | Kroll et al. .................. 600/391 |
| 5,265,579 A | | 11/1993 | Ferrari |
| 5,402,780 A | * | 4/1995 | Faasse, Jr. ................... 600/392 |
| 5,785,040 A | * | 7/1998 | Axelgaard .................... 600/391 |
| 6,360,119 B1 | | 3/2002 | Roberts |
| 6,950,688 B2 | * | 9/2005 | Axelgaard et al. ........... 600/391 |
| 7,085,598 B2 | * | 8/2006 | Sato et al. ................... 600/372 |
| 2002/0107435 A1 | | 8/2002 | Swetlik et al. |
| 2003/0040788 A1 | | 2/2003 | Dupelle et al. |
| 2004/0039275 A1 | | 2/2004 | Sato et al. |
| 2004/0176674 A1 | | 9/2004 | Nazeri |
| 2007/0088227 A1 | | 4/2007 | Nishimura |

FOREIGN PATENT DOCUMENTS

| | | | | |
|---|---|---|---|---|
| GB | 2240928 | * | 8/1991 | .................... 600/392 |
| JP | 2004-97809 | | 4/2004 | |
| JP | 2004-121360 | | 4/2004 | |
| RU | 2028077 | | 2/1995 | |
| RU | 2086176 | | 8/1997 | |

OTHER PUBLICATIONS

Russian Decision on Grant issued in Russian Application No. 2006128834 (including a partial translation thereof).
Katonov et al., Balneal Cardiomonitor KMB-01, Medical Equipment Magazine, No. 2, 1982, pp. 23-24 (partial English translation attached).
European Office Action dated Mar. 11, 2008 issued in EP Application No. 06118538.5.

* cited by examiner

*Primary Examiner* — Lee S Cohen
(74) *Attorney, Agent, or Firm* — Drinker Biddle & Reath, LLP

(57) ABSTRACT

A waterproof bioelectrode includes an electrode pad (101) to be mounted on a living body and a lead wire (110) to be connected to the electrode pad. The electrode pad includes a waterproof base (106) having an adhesive contacting surface and a hole substantially at its center, a waterproof seal member (105) which fixes the lead wire to a lower surface of the contacting surface of the base while covering the hole such that a detection electrode provided to a distal end of the lead wire is exposed from the hole of the waterproof base, and a conductive gel (103) arranged on the contacting surface to come into contact with the detection electrode.

6 Claims, 9 Drawing Sheets

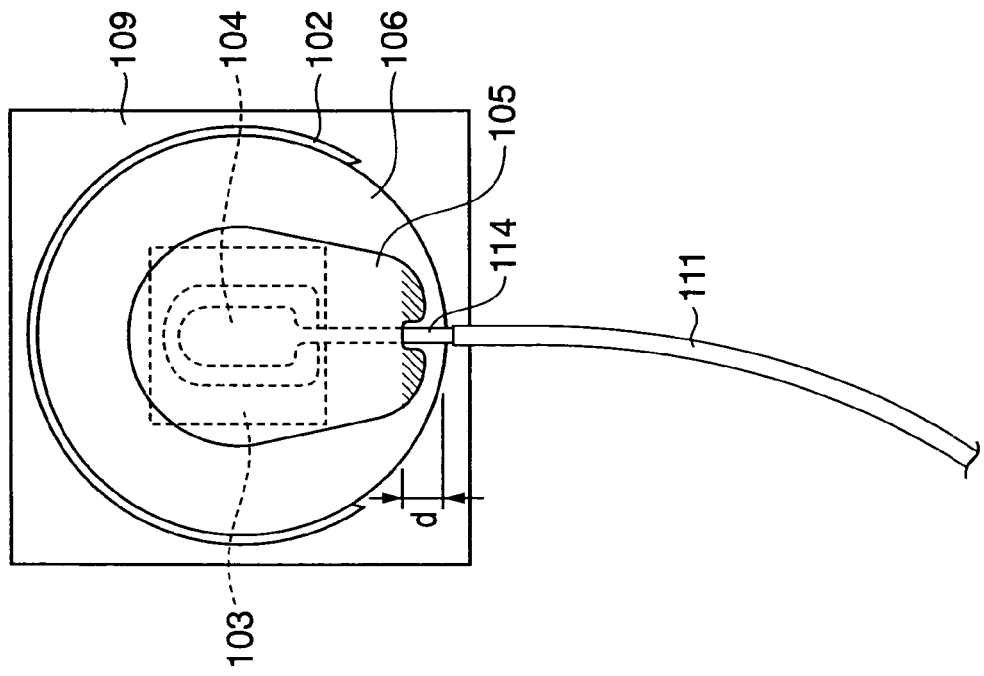
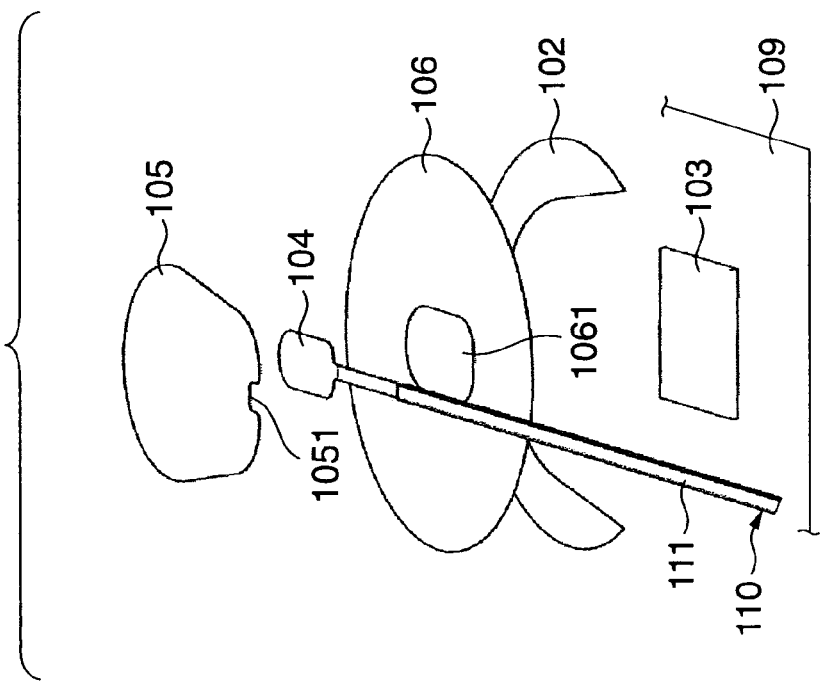

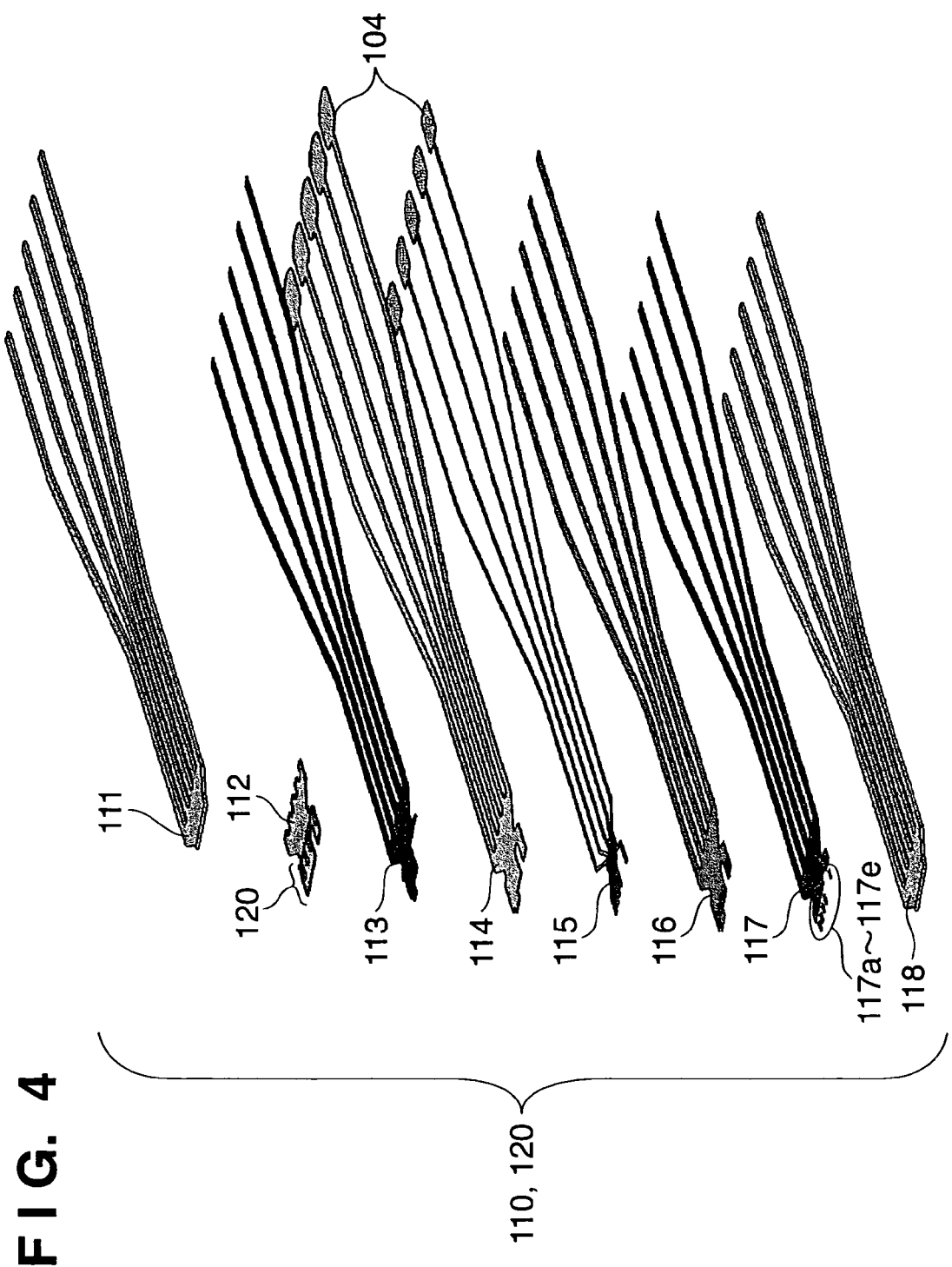

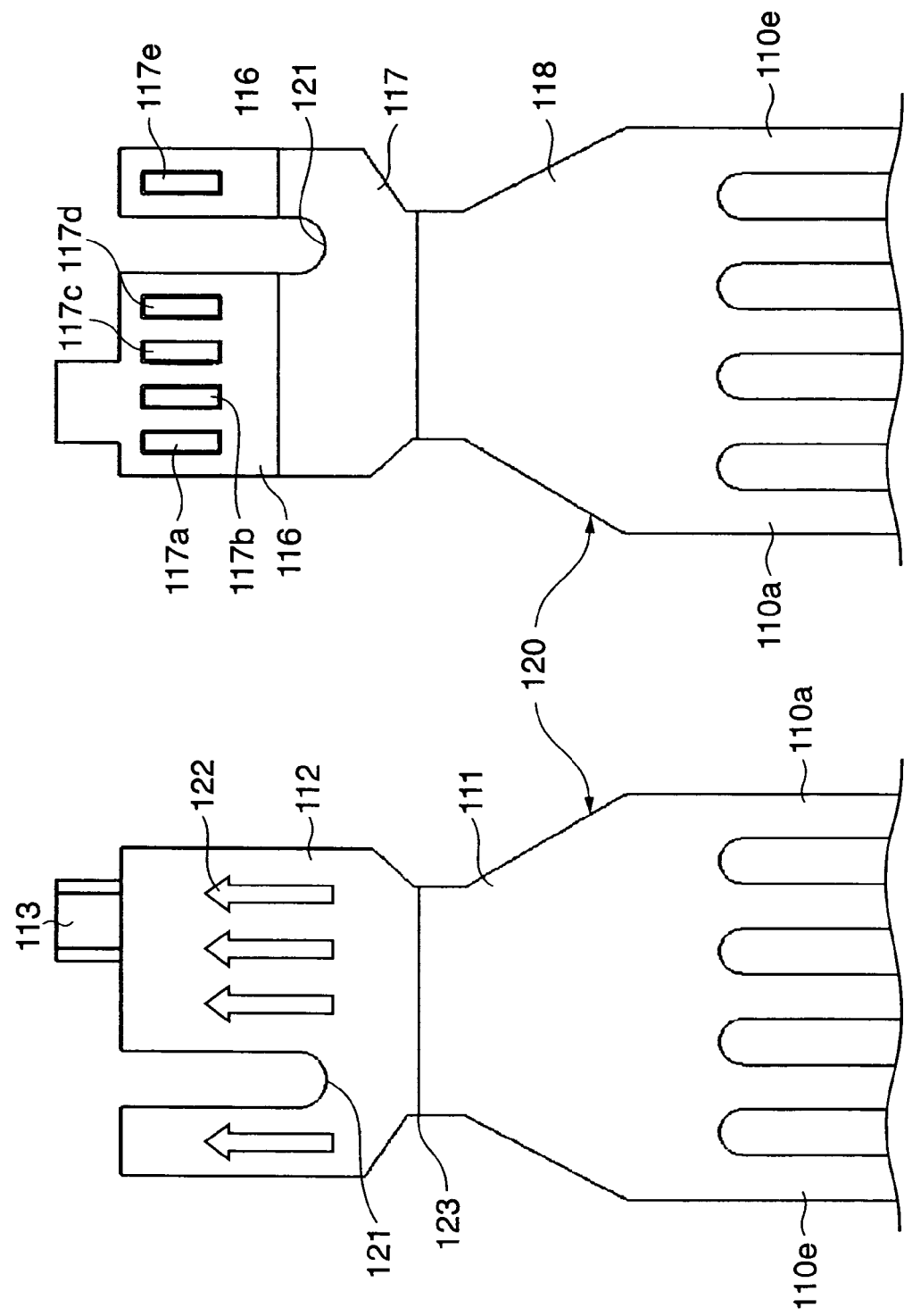

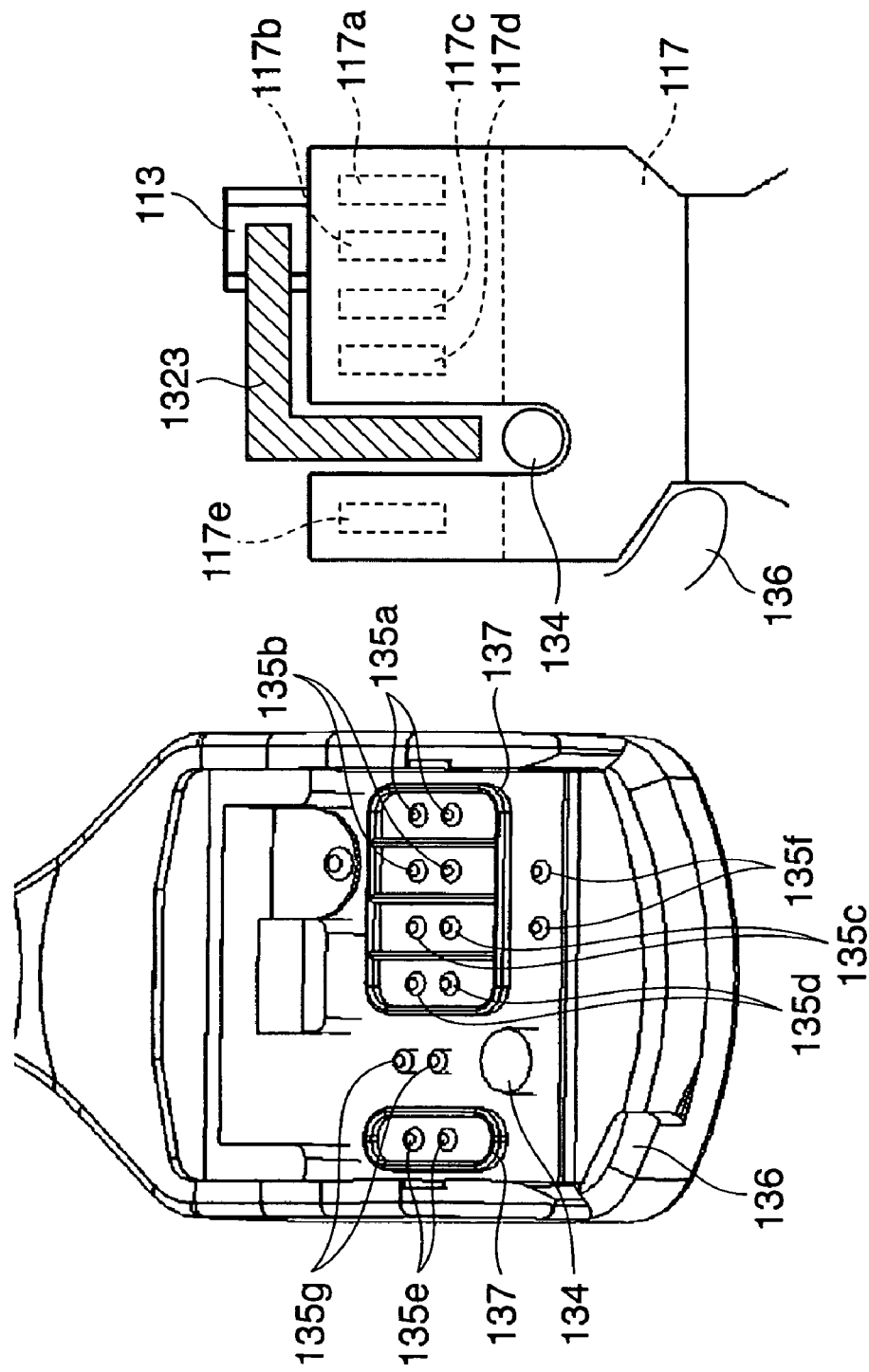

WATERPROOF BIOELECTRODE

CLAIM OF PRIORITY

This application claims priority from Japanese Patent Application No. 2005-231083, filed on Aug. 9, 2005, which is hereby incorporated by reference herein.

BACKGROUND OF THE INVENTION

1. Field of the Invention

The present invention generally relates to an electrode for acquiring a biomedical signal (bioelectrode) and, more particularly, to a waterproof bioelectrode.

2. Description of the Related Art

Conventionally, a biomedical signal typically represented by an electrocardiogram is widely used as information useful for diagnosis. A biomedical signal may be acquired not only in at rest but also during exercise or daily life depending on its purpose. For example, acquisition of an electrocardiogram by a Holter electrocardiograph is a typical way of acquiring a biomedical signal during daily life for a long period of time continuously.

To acquire a biomedical signal, a bioelectrode to be attached on the body surface is necessary. The bioelectrode must acquire a stable biomedical signal with small noise over an acquisition period. For this purpose, a wide variety of bioelectrodes are available in accordance with the type of the biomedical signal to be acquired, the acquisition environment, the acquisition period, and the like.

In acquisition of the biomedical signal by means of the Holter electrocardiograph described above, the bioelectrode must follow the body motion accompanying the daily life of the object and be kept firmly attached on the body surface without peeling by perspiration over a long period of time.

A conventionally used bioelectrode is generally non waterproof and the position where the electrode is attached influences the quality of the biomedical signal. Therefore, even a biomedical signal acquisition by means of the Holter electrocardiograph may last for two days, the object is often prohibited taking a bath or shower during measurement. If the object must necessarily take a bath or shower, the electrode is removed temporarily in advance and re-attached afterwards. To remove and re-attach the electrode, however, bothers the object. Further, in re-attaching, the attaching position may be shifted, or the electrode may not be correctly attached in tight contact with the body surface. This may influence the biomedical signal to be acquired to interfere with accurate diagnosis. Therefore, it is desirable that the electrode need not be removed even if the electrode portion may get wet while the object takes a bath or shower.

When taking a bath or shower, the burden to the heart increases, and accordingly an abnormality may occur in the electrocardiogram. If the electrocardiogram in such an abnormal state cannot be acquired, information that is critical in diagnosis may be overlooked. Hence, a waterproof electrode is desirable also from the viewpoint of enabling acquisition of biomedical signals in various states. Accordingly, waterproof bioelectrodes have been proposed (see Japanese Patent Laid Open Nos. 2004-121360 (D1) and No. 2004-097809 (D2)).

According to the bioelectrode described in D1, an electrocardiogram is acquired with one electrode pad. A plurality of electrodes are necessary to obtain a biomedical signal, and a short distance between electrodes is undesired to obtain a signal having a good quality. For this reason, a certain amount of distance must be ensured between two electrodes provided to the pad, leading to a large size pad. It is not easy to attach a large size sheet in tight contact with the body surface. In addition, because a large-size sheet cannot easily follow the body motion, a gap tends to be formed between the sheet and the body surface. Hence, it is hard to maintain waterproofness.

Further, the bioelectrode pad described in D1 has a signal processing circuit, which transmits a signal to a monitor device by radio communication and is directly connected to the electrode pad. Hence, the electrode has a large projection to make the object who wears it feel uncomfortable. Also, the signal processing circuit portion may be pulled by the clothes or underwear of the object. Moreover, since the signal processing circuit must transmit a biomedical signal by radio communication, it requires a power supply and accordingly power supply management.

In the bioelectrode described in D2, a cable is connected to the electrode using a connector. The connector is connected adjacent to the electrode, and a large projection is present in the vicinity of the electrode, in the same manner as in D1. Hence, the object who wears the bioelectrode feels uncomfortable, and when the projection abuts against the electrode, noise may be superposed on the biomedical signal, which are the same problems as those in D1.

In both patent references 1 and 2, a sheet made of a polyethylene foam or polyurethane foam is used as the material of the electrode pad. Although external water will not be permeated through the electrode pad, moisture from inside (the body surface of the object) generated by perspiration is not transpired either. Consequently, the attaching portion of the body surface becomes sweaty during a long period use and may cause an itch or the like.

SUMMARY OF THE INVENTION

The present invention has been made in view of the problems of the prior art and has as its object to provide a bioelectrode with comfortable wearability and good waterproofness.

That is, a gist of the present invention lies in a waterproof bioelectrode comprising an electrode pad to be attached on a living body and a lead wire to be connected to said electrode pad, characterized in that said electrode pad comprises: a waterproof base member having an adhesive contacting surface and a hole substantially at a center thereof, a waterproof seal member which fixes said lead wire to a back surface of said base, wherein said back surface is opposite to said contacting surface, while covering the hole such that a detection electrode provided to a distal end of said lead wire is exposed through the hole of said waterproof base, and a conductive gel arranged on said contacting surface of said base to come into contact with said detection electrode.

With this arrangement, the waterproof bioelectrode according to the present invention can satisfy both comfortable wearability and waterproofness.

Other objects and advantages besides those discussed above shall be apparent to those skilled in the art from the description of a preferred embodiment of the invention which follows. In the description, reference is made to accompanying drawings, which form a part thereof, and which illustrate an example of the various embodiments of the invention. Such example, however, is not exhaustive of the various embodiments of the invention, and therefore reference is made to the claims which follow the description for determining the scope of the invention.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 3A and 3B show views for explaining the arrangement of an electrode pad portion in the bioelectrode of the embodiment of FIG. 1.

FIG. 4 is an exploded perspective view showing an arrangement of the lead wires and connector in the bioelectrode of the embodiment of FIG. 1.

FIGS. 5A and 5B show views showing a detailed arrangement of the connector portion in the bioelectrode of the embodiment of FIG. 1.

FIGS. 8A and 8B show views for explaining the arrangement of electrode pins provided to the housing 133 and the positional relationship among them when the connector 120 is mounted in the housing 133.

DESCRIPTION OF THE EMBODIMENTS

Preferred embodiments of the present invention will be specifically described below in accordance with the accompanying drawings.

The preferred embodiment of the present invention will be described below in detail with reference to the accompanying drawings.

Figure 1:
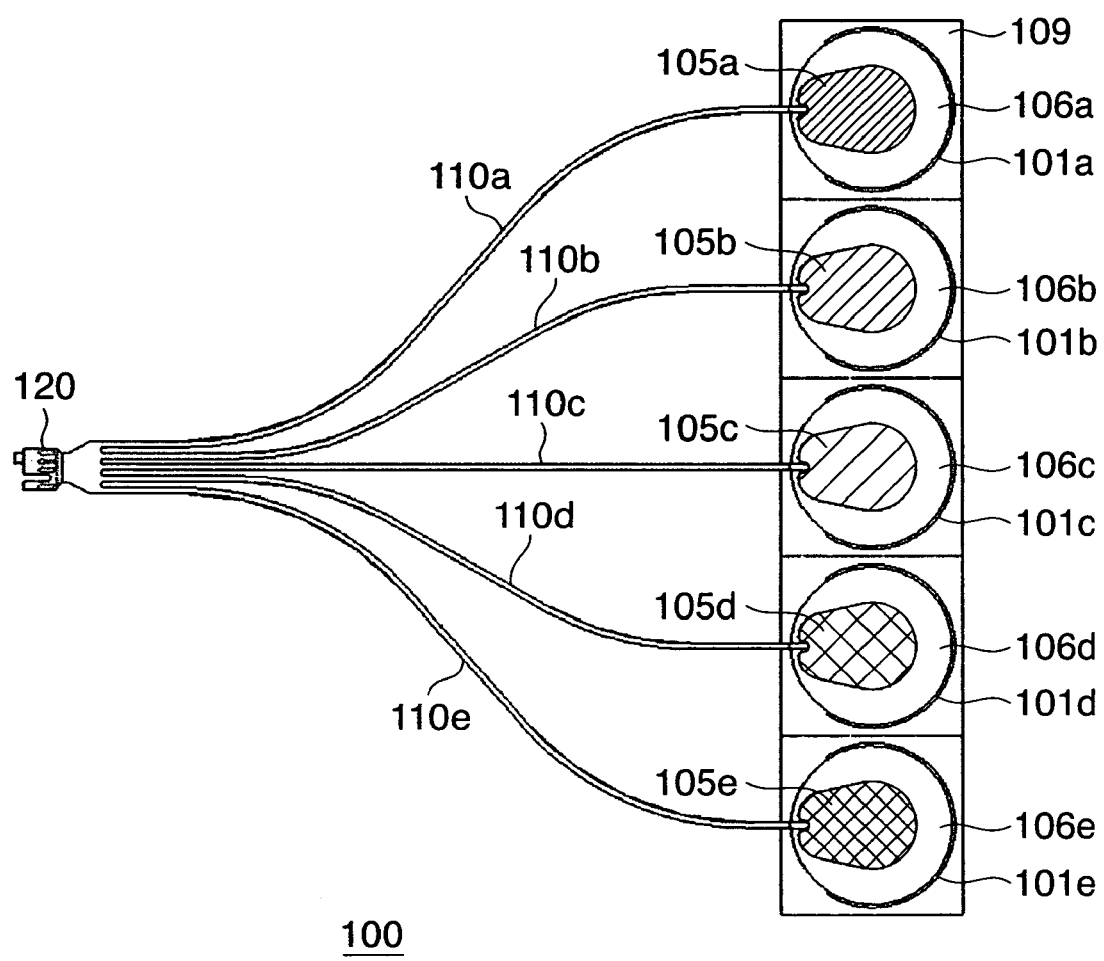
FIG. 1 is a plan view showing an overall arrangement of a bioelectrode according to an embodiment of the present invention.

FIG. 1 is a plan view showing an overall arrangement of a bioelectrode according to an embodiment of the present invention. Referring to FIG. 1, a bioelectrode 100 has five electrode pads 101a to 101e, a connector 120, and lead wires 110a to 110e which connect the connector 120 to the corresponding electrode pads 101a to 101e. The back surfaces of the electrode pads 101a to 101e (bases 106a to 106e) are adhesive and accordingly provided with a first separator 109 serving as a release paper.

In this embodiment, the separator 109 is shared by the all electrode pads 101a to 101e, and has perforations for separation. Alternatively, the separator 109 may be provided to each electrode pad. The number of electrodes is not limited to five but can be any other arbitrary number such as three, seven, or the like.

Seal members 105a to 105e are adhesive moisture-permeable waterproof films and adhered to the base 106 of the electrode pads 101a to 101e to cover the portions around the distal ends of the lead wires 110a to 110e. With the seal members 105a to 105e, the lead wires 110a to 110e are connected to the electrode pads 101a to 101e in a watertight manner.

According to this embodiment, the electrode pads are colored by coloring the seal members 105a to 105e In the following description, when an arrangement shared by the electrode pads 101a to 101e is to be described or the electrode pads 101a to 101e as a whole are to be described, the electrode pads 101a to 101e may be merely expressed as the electrode pad 101. This applies to the seal members 105a to 105e and the like.

Figure 2:
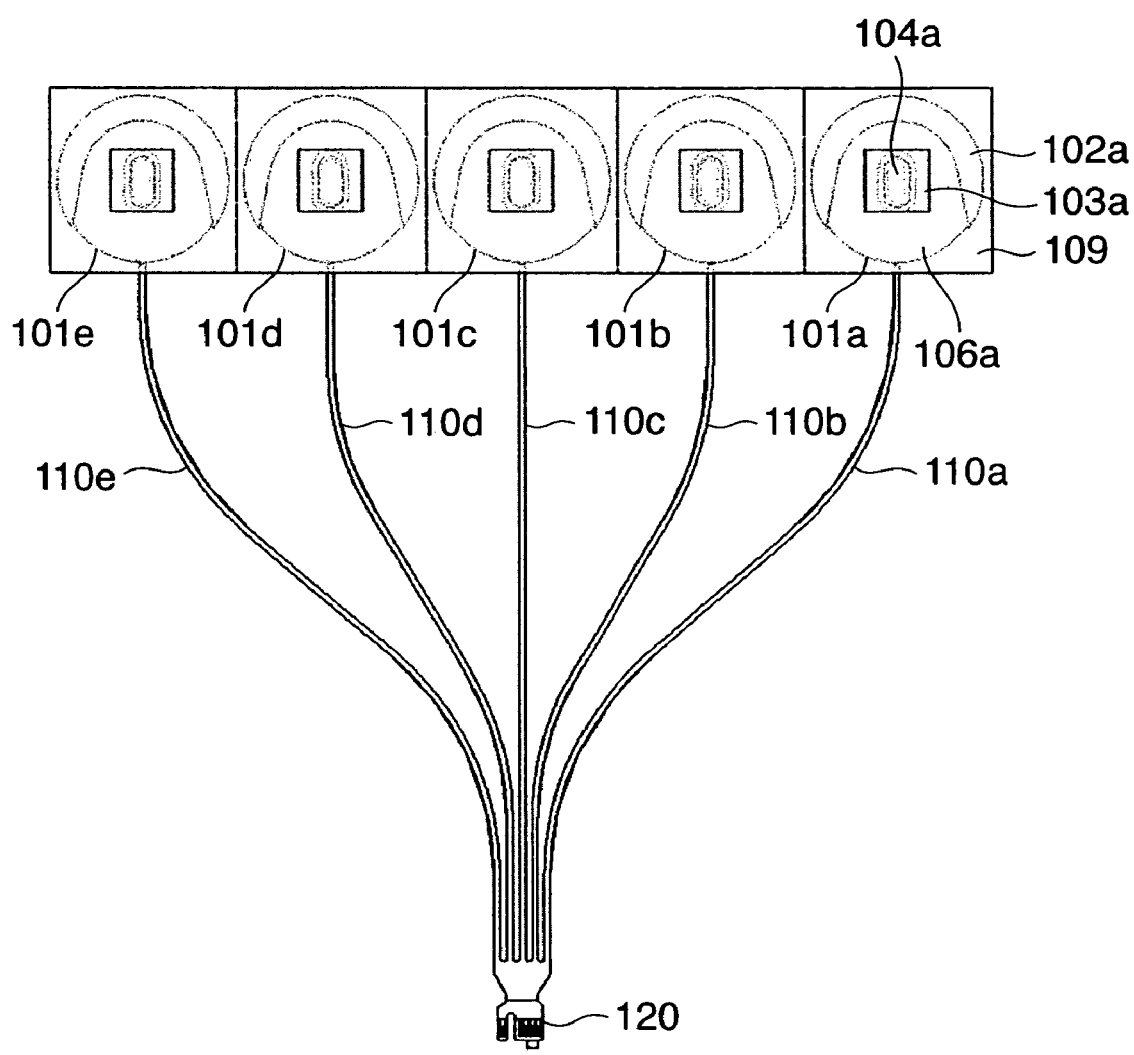
FIG. 2 is a bottom view showing an overall arrangement of the bioelectrode according to the embodiment of FIG. 1 of the present invention.

FIG. 2 is a bottom view of an arrangement of the bioelectrode according to this embodiment. The same constituent elements as those in FIG. 1 are denoted by the same reference numerals. In FIG. 2, the lower surfaces (surfaces on a side to come into contact with the body surface; to be referred to as contacting surfaces as well) of the electrode pads 101a to 101e are seen through the first separator 109.

The electrode pad 101a will be typically explained. A second separator 102a is arcuate release paper arranged at the outer border of the contacting surface. The second separator allows the base 106 made of the moisture-permeable waterproof film to be peeled from the first separator 109 easily and also serves as a support agent to support the base 106 as maintaining its shape.

A conductive adhesive gel 103a is a member to electrically connect the distal end of the lead wire 110a which serves as a detection electrode 104a to the surface of the living body. Conventionally used conductive adhesive gel can be used as the conductive adhesive gel 103a.

FIGS. 3A and 3B show views for explaining the arrangement of an electrode pad portion in the bioelectrode according to this embodiment, in which FIG. 3A is an exploded perspective view, and FIG. 3B is a plan view.

The distal end of the lead wire 110 forms the detection electrode 104. The detection electrode 104 and a portion around it are not provided with foam materials 111 and 118 to be described later. Since no foam materials 111 and 118 are provided to portions that are to be fixed by the seal member 105, these portions are very thin, so the lead wire 110 can be attached to the base 106 while ensuring waterproofness with the seal member 105. The base 106 which forms most of the electrode pad 101 is formed of a moisture-permeable waterproof film and has a hole 1061 substantially at its center.

An adhesive is applied to the contacting surface of the base 106, and the arcuate second separator 102 is arranged at the outer border of the contacting surface. The second separator is a release paper, and its surface opposing the first separator 109 is not adhesive. Therefore, that region of the contacting surface of the base 106 where the second separator 102 is present can be readily separated from the first separator 109.

In order to realize the waterproofness, the bioelectrode according to this embodiment uses the moisture-permeable waterproof film as the base 106. The flexible moisture-permeable waterproof film member is used because the moisture from the skin is transpired to improve the adhesion with respect to the skin, and because the film member is deformable to follow the wrinkles or the like of the skin formed by body motion. The thickness of the moisture-permeable waterproof film that can be used as the base 106 is preferably 20 μm to 70 μm, more preferably 30 μm to 60 μm, particularly preferably 40 μm to 60 μm, and most preferably 45 μm to 55 μm.

If the moisture-permeable waterproof film is excessively thick, the effect of transpiring the moisture from the skin cannot be sufficiently obtained, so the film tends to be peeled easily. In addition, the film may cause the skin to develop a rash or to become humid to degrade the comfortableness of the object who wears the electrode pad. As the flexibility (particularly the followability with respect to the wrinkles of the skin surface) degrades, the stiffness of electrode become perceivable as uncomfortable, the waterproofness may degrade, and the electrode can be peeled easily. Further, as the flexibility degrades, the biomedical signal may likely to include noise.

On the other hand, using the flexible thin film base 106 arises difficulty of attaching of the electrode on the skin. This can be easily imagined when considering a case wherein, e.g., a protection film is to be adhered to glass. More specifically, since the base 106 is not stiff (has low rigidity), when peeling the base 106 from the first separator 109, the contacting surfaces of those portions which are not held by the fingers may adhere to each other, and wrinkles form easily when attaching the electrode.

In order to solve these problems, in the bioelectrode of this embodiment, the arcuate second separator 102 is arranged at the outer border of the contacting surface of the base 106. When the base 106 is to be peeled from the first separator 109 by the second separator 102, the thin base 106 can be peeled more easily than by a nail or the like. As the second separator 102 is arcuately arranged along the outer border, the electrode pad 101 (base 106) can be peeled from the first separator 109 while the base 106 almost maintains its shape.

The second separator 102 is made of a comparatively stiff material such as release paper. Accordingly, when the second separator 102 is pinched, the base 106 will not bend to cause its contacting surface portions to adhere to each other, but can be maintained spread. In this manner, the second separator 102 also serves as the support member for the electrode pad 101 since the electrode pad 101 is peeled from the first separator 109 until it is attached on the body surface.

The material, thickness, and shape of the second separator 102 are not particularly limited as far as it can maintain the base 106 in the spread state when the electrode pad 101 is separated from the first separator 109. However, considering the convenience in use when separating the electrode pad 101 from the first separator 109, the second separator 102 preferably supports the outer border of the base 106 throughout a predetermined length.

For example, the separator 102 can be arranged throughout the entire circumference of the outer border of the base 106. Note that the second separator must be removed finally. When considering the convenience in use when attaching the electrode pad 101 to the body surface, the second separator should not preferably be excessively long. For this reason, when arranging the separator throughout the entire circumference of the outer border, the separator may not be formed as one continuous separator but be preferably formed to be dividable into a plurality of portions by forming cuts so it can be removed easily. In this case, if an incision is formed at the position corresponding to the lead wire 110, the separator can be removed easily, which is preferable.

In this manner, the length of the second separator may be determined appropriately within such a range that it can serve as the support member considering the size and material of the base 106, the material and width of the second separator, and the like. When a very flexible material is to be used to form the base 106, the second separator is preferably provided to cover about half the circumference of the outer border so it can serve as the support member.

The first separator 109 formed of, for example, a PET film is provided with the conductive gel 103. In this embodiment, the size of the hole 1061 in the base 106 is smaller than that of the conductive gel 103. The conductive gel 103 adheres to the base 106 with an adhesive applied to the contacting surface of the base 106. When the electrode pad 101 is to be separated from the first separator 109, the conductive gel 103 is separated from the first separator 109 together with the base 106.

The seal member 105 is formed of, for example, the same moisture-permeable waterproof film as that of the base 106. The seal member 105 is provided to protect the detection electrode 104 arranged at the distal end of the lead wire 110 from entering water. The seal member 105 is preferably large from the viewpoint of enhancing the waterproofness of the detection electrode 104. On the other hand, from the viewpoint that the flexibility of the seal member 105 degrades at a portion overlapping the base 106 and that the moisture generated by the skin must be transpired quickly, the seal member 105 is preferably small. Therefore, the seal member 105 is desirably made small within a range that the waterproofness can be maintained.

For this reason, according to this embodiment, as the portion around the hole 1061 can be easily maintained in tight contact with the base 106, the seal member 105 is slightly larger than the hole 1061. On the other hand, regarding the portion to seal the lead wire 110 which is thick, the seal member 105 has a sufficient length to seal around the lead wire 110. A notch 1051 substantially corresponding to the sectional shape of the lead wire 110 is formed in the seal member 105 in order to prevent water from entering from the side surface of the lead wire 110.

When the notch 1051 is set to correspond to the lead wire 110 and the seal member 105 is adhered to the surface of the base 106, the gap between the lead wire 110 and seal member 105 is eliminated, so water entering can be prevented effectively. Body motion or the like applies a load on the connecting point of the lead wire 110 and electrode pad 101. Therefore, the seal member 105 is designed to have a large area relative to the width of the lead wire 110, so sufficient adhesive force can be obtained. Due to the presence of the notch 1051, the seal member 105 extends round to cover a portion before the connection start position of the lead wire 110. Hence, the adhesive force of the hatched region of the seal member 105 provides a large resistance against the force that pulls the lead wire 110.

The lead wire 110 is fixed to the base 106 at a portion slightly inside the outer circumference of the base 106 (in FIG. 3B, a location inside the outer circumference by a distance d) by the seal member 105. Therefore, when the lead wire 110 is pulled, the edge of the base 106 will not be pulled. Accordingly, the seal member 105 can be prevented from peeling from the edge of the base 106 when the lead wire 110 is pulled.

In this manner, the seal member 105 has the function of fixing the detection electrode 104 to a position corresponding to the hole 1061, the function of protecting the detection electrode 104 (strictly, that entire portion of the distal end of the lead wire 110 where the conductive pattern is exposed) from entering water, and the function of fixing the lead wire 110 to the base 106 against the load such as the tension acting on the lead wire 110.

When attaching the electrode pad 101, first, the electrode pad 101 is separated from the first separator 109 using the second separator 102. While supporting the electrode pad 101 by the second separator 102, the electrode pad 101 is moved to the contacting target portion and adhered to the body surface from its outer border where the second separator is not provided. The entire surface of the base 106 is brought into tight contact with the body surface while peeling the second separator 102.

FIG. 4 is an exploded perspective view showing an arrangement of the lead wires and connector in the bioelectrode according to this embodiment.

In this embodiment, lead wires 110 and a connector 120 are formed on a common base. Referring to FIG. 4, a base 114 is formed of, e.g., a PET film. An electrode pattern 115 made of AgCl is formed on the lower surface (the surface that opposes the body surface when the electrode is attached) of the base 114 by, e.g., printing. A resist pattern 116 to insulate the electrode pattern 115 is also formed on the lower surface of the electrode pattern 115 by printing. In order for destaticizing, a lower shield pattern 117 and an upper shield pattern 113 each made of a conductive material are formed on the lower surface of the resist pattern 116 and the upper surface of the base 114, respectively, by printing. A reinforcing base 112 formed of, e.g., a PET film, is adhered to the apparatus side end of the upper surface of the upper shield pattern 113. An upper foam material 111 and a lower foam material 118 each made of a water non permeable flexible insulating material (foamed material sheet) are arranged on the uppermost surfaces and lowermost surfaces of the lead wires 110 with adhesives. The foam material provides appropriate flexibility and rigidity to the lead wires 110.

Of these members, those excluding the base 114 and electrode pattern 115 which constitute detection electrodes 104 cover as far as portions slightly before the detection electrodes 104, as shown in FIGS. 3A and 3B. The upper and lower foam materials 111 and 118 have lengths to cover as far as portions on the apparatus side before the connector portions. In FIG. 4, the portion which corresponds to a predetermined region on the near side of the reinforcing base 112 serves as the connector 120.

Small regions 117a to 117e are provided as part of the lower shield pattern 117. The small regions 117a to 117e are provided to protect the signal reading out portion of the electrode pattern 115, as will be described later. Therefore, their object and function are different from the primary object and function of the lower shield pattern 117.

The lead wire portions and connector portion shown in FIG. 4 can be formed by sequentially forming the respective layers and punching out the whole layers into the outer shape of the base 114.

FIGS. 5A and 5B show views showing a detailed arrangement of the connector portion in the bioelectrode according to this embodiment, in which FIG. 5A is a plan view, and FIG. 5B is a bottom view.

As described above, an upper foam material 111 and lower foam material 118 are provided to extend as far as before the end of the connector portion. When seen from above, for a portion where the upper foam material 111 is not provided, a reinforcing base 112, the distal end of an upper shield pattern 113, and a base 114 around the distal end of the upper shield pattern 113 are exposed.

When seen from below, for a portion where the lower foam material 118 is not provided, a lower shield pattern 117 and resist pattern 116 are exposed. Of the lower shield pattern 117, small regions indicated by reference numerals 117a to 117e protect regions where biomedical signals are to be read out. Hence, the small regions 117a to 117e are not covered by the lower resist pattern 116 and are in contact with the end of the electrode pattern 115. Accordingly, signals from individual detection electrodes 104 can be read out through the small regions 117a to 117e.

A notch 121 is formed in the connector 120. With the notch 121, the flat plate like connector 120 can be mounted in a connector mounting portion (to be described later) only in the correct direction.

A narrow portion 123 is formed at least one side of the connector 120. The narrow portion 123 fits with a projection formed on the connector mounting unit, when mounted on the connector mounting unit to be described later, to prevent the connector 120 from being pulled out carelessly.

Figure 6:
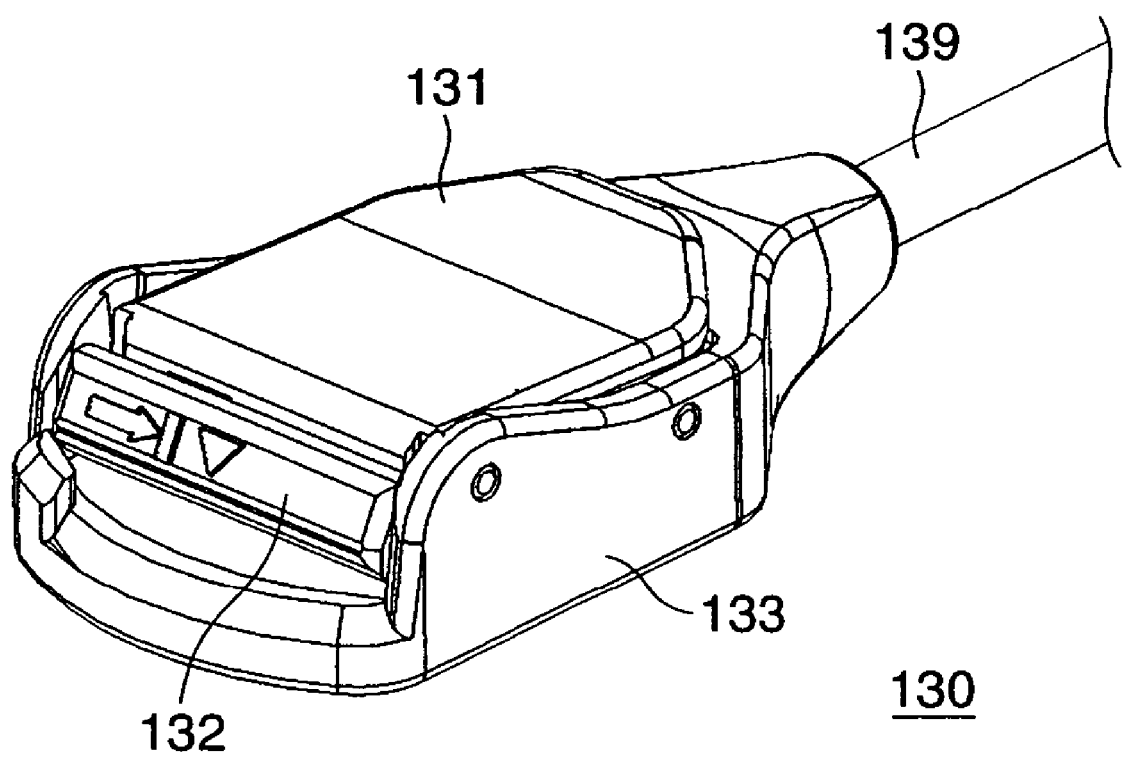
FIG. 6 is a perspective view showing an arrangement of the connector mounting unit of an intermediate cable which connects the connector 120 to a biomedical signal acquisition apparatus (not shown).

FIG. 6 is a perspective view showing an arrangement of the connector mounting unit of an intermediate cable (bioelectrode connection cable) which connects the connector 120 to a biomedical signal acquisition apparatus (not shown). The other end of the intermediate cable is directly connected to the biomedical signal acquisition apparatus. Alternatively, the other end of the intermediate cable is provided with an apparatus connector (not shown) which corresponds to the connector of the biomedical signal acquisition apparatus. The intermediate cable connects the apparatus connector to the connector of the biomedical signal acquisition apparatus.

Roughly speaking, a connector mounting unit 130 has a housing 133, pressure plate 132, and lever 131. Electrode pins (to be described later) arranged in the housing 133 are connected to a cable 139 to transmit biomedical signals to the apparatus side.

Figure 7:
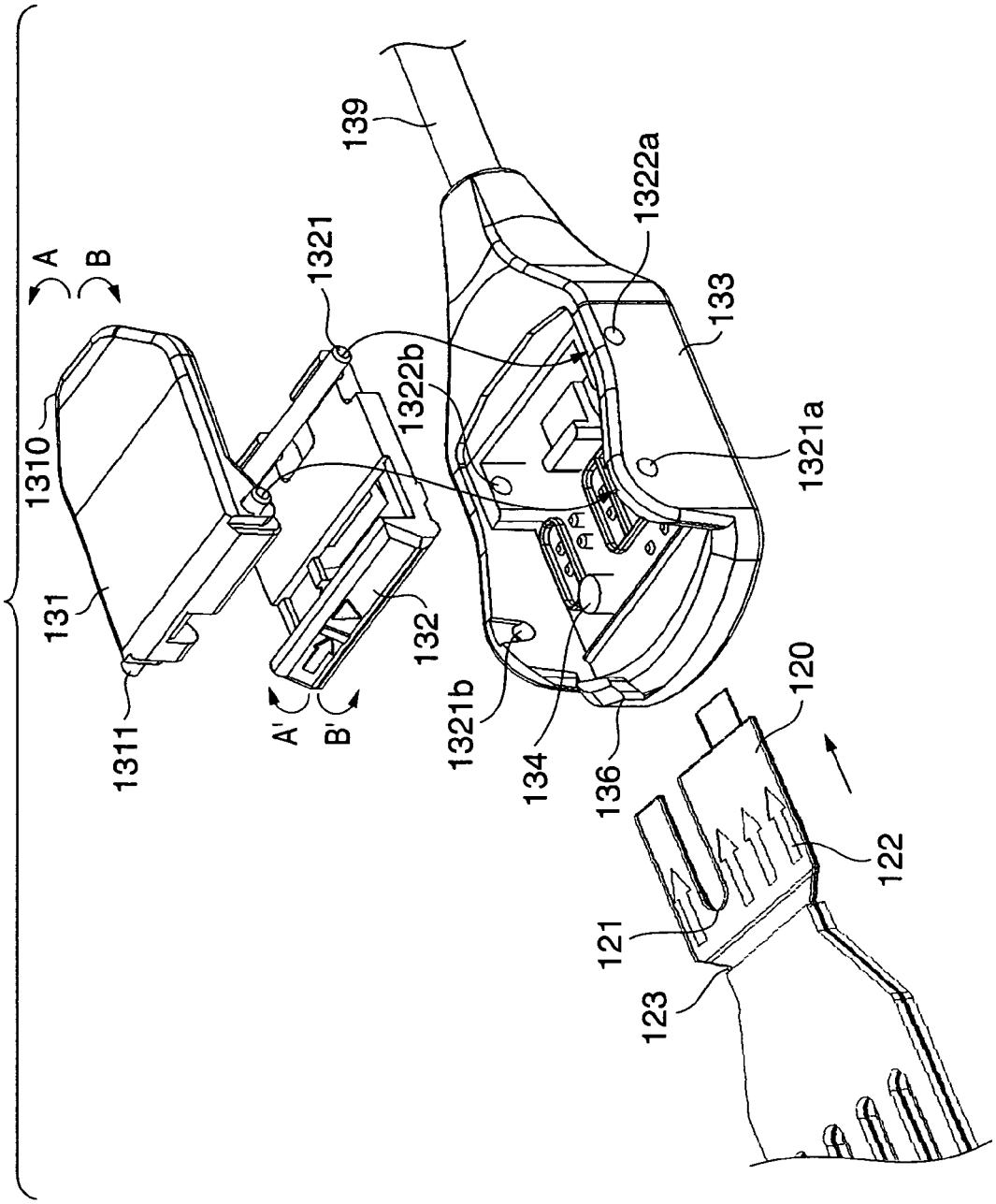
FIG. 7 is a perspective view for explaining the internal arrangement and mechanism of the connector mounting unit 130 and a method of mounting the connector 120 of the bioelectrode 100.

FIG. 7 is a perspective view for explaining the inner arrangement and mechanism of the connector mounting unit 130 and a method of mounting the connector 120 of the bioelectrode 100.

FIG. 7 shows the connector mounting unit 130 using an exploded perspective view to facilitate understanding of the mutual relationship and mutual operation among the lever 131, pressure plate 132, and housing 133 of the connector mounting unit 130.

The electrode pins are arranged on the bottom surface of the housing 133. The electrode pins come into contact with the shield pattern 117 exposed to the lower surface of the connector 120 to read out signals, or for grounding. A protrusion 134 which enables insertion of the connector only in the correct direction is also arranged on the bottom surface of the housing 133. The bioelectrode 100 according to this embodiment has marks (arrows in this case) on its surface that forms the upper surface when the lever 131 of the connector mounting unit 130 is located on the upper side. The marks serve as the indices of the direction when the connector 120 is to be mounted in the connector mounting unit 130.

A projection 136 is formed at the mouth of the housing 133. The projection 136 is arranged at such a position that when the connector 120 is inserted in the correct direction and the protrusion 134 has reached the deepest end of the notch 121 formed in the connector 120, the narrow portion 123 of the connector 120 fits with the projection 136. As will be described later, when the lever 131 is lowered in this condition and a force to press the connector 120 is applied to the housing 133 through the pressure plate 132, the narrow portion 123 catches on the projection 136, so the connector 120 can be prevented from being pulled out carelessly.

The pressure plate 132 is attached to holes 1322a and 1322b formed in the rear end of the housing 133 to be pivotal upward (arrow A') and downward (arrow B') about a shaft 1321, provided to the rear end (the side where the cable 139 is connected) of the pressure plate 132, as a rotating shaft.

The lever 131 is attached to holes 1321a and 1321b formed in the front end of the housing 133 to be pivotal upward (arrow A) and downward (arrow B) about a shaft 1311, provided to the front end of the lever 131, as a rotating shaft.

When a manipulating portion 1310 of the lever 131 is pulled upward (in the direction of the arrow A), the front end of the pressure plate 132 is released and moved upward (in the direction of the arrow A'). This enables the connector 120 of the bioelectrode 100 to be inserted in the housing 133. This state of the connector mounting unit 130 is called a connector mountable state.

When the manipulating portion 1310 of the lever 131 is pushed downward (in the direction of the arrow B) to be set in the state shown in FIG. 6, it presses the front end of the pressure plate 132 downward (in the direction of the arrow B'). In this state, the connector 120 cannot be inserted in the housing 133. If the connector 120 has already been inserted in the housing 133, the connector 120 is urged against the electrode pins (to be described later) in the housing 133 by the pressure plate 132.

At this time point, the narrow portion 123 of the connector 120 firmly fits with the projection 136 of the housing 133 to prevent the connector 120 from being pulled out carelessly.

FIGS. 8A and 8B show views for explaining the arrangement of the electrode pins provided to the housing 133 and the positional relationship among them when the connector 120 is mounted in the housing 133.

As shown in FIG. 8A, seven pairs of electrode pins 135a to 135g are provided to the bottom surface of the housing 133 of the connector mounting unit 130 of this embodiment. The respective electrode pins 135a to 135g are connected to the cable 139 through wiring lines in the housing 133.

FIG. 8B is a view seen from above of a state wherein the connector 120 is correctly mounted in the connector mounting unit 130. As is apparent from comparison of FIGS. 8A and 8B, the electrode pins 135a to 135f are arranged at positions to come into contact with the lower shield pattern 117 (including the small regions 117a to 117e aimed at protecting the electrode pattern 115) exposed to the lower surface of the connector 120.

More specifically, the electrode pins 135a to 135e are arranged at positions to come into contact with the small regions 117a to 117e (that is, the individual electrode patterns 115). The electrode pins 135f are in contact with the main body (a portion excluding the small regions 117a to 117e) of the lower shield pattern 117 to ground the lower shield pattern 117.

The remaining electrode pins 135g are provided to ground the upper shield pattern 113. Note that the upper shield pattern 113 is exposed from the distal end of the upper surface of the connector 120. Hence, an electrical connection plate 1323 made of a conductive material is arranged on the lower surface of the pressure plate 132, so the electrode pins 135g are electrically connected to the upper shield pattern 113 exposed to the upper surface of the connector 120 through the pressure plate 132.

As described above, the entire bioelectrode according to this embodiment is disposable. Hence, a sanitary bioelectrode 100 can always be used. Since the signal is transmitted using the lead wire 110, a signal processing circuit which performs a complicated process such as radio communication need not be attached to the electrode pad. The electrode pad 101 is thus substantially flat and can be mounted on the body surface with comfortable wearability.

As the flexible moisture-permeable waterproof films are used to form the base 106 and seal member 105, the bioelectrode can be bright into tight contact with the body surface well to realize high waterproofness. Also, moisture from the body surface can be transpired quickly. The object's skin does not become sweaty or a rash does not develop easily to make the object feel comfortable. In addition, the bioelectrode is not peeled readily.

As the second separator is provided to the outer border of the base 106, the electrode pad 101 can be readily separated from the first separator 109. As the base 106 can be supported by the second separator, the contacting surface portions of the base 106 will not adhere to each other, and wrinkles can be prevented when attaching the bioelectrode. This is particularly effective when a highly adhesive film member is used as the base 106.

As the lead wire 110 has a film-like shape and is thin, it can be easily fixed to the base 106 with waterproofness by the seal member 105.

In the embodiment described above, only a case wherein the lead wires 110 have the same length has been described in order to facilitate the description and understanding. When biomedical signals to be acquired are known in advance, the lead wires can have different lengths depending on their attaching positions.

Figure 9A:
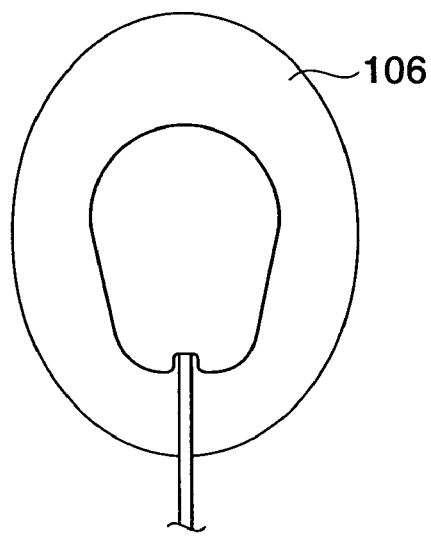
FIGS. 9A to 9D show views showing other shapes of the base 106.
Figure 9B:
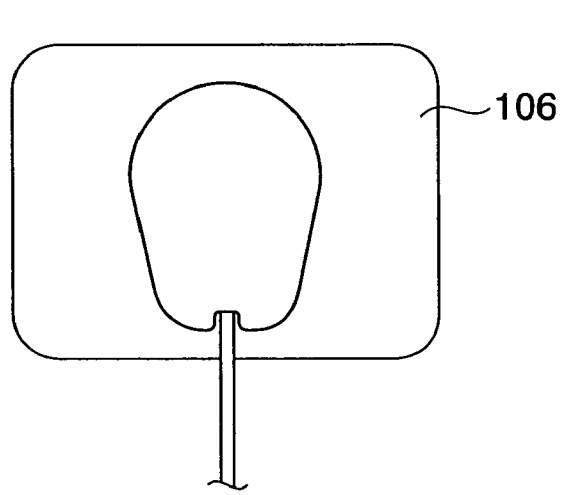
Figure 9C:
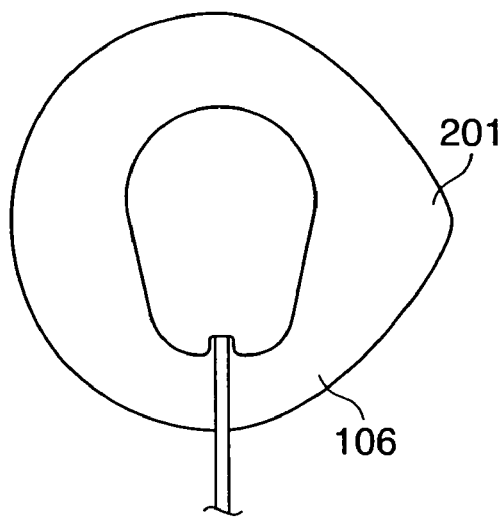
Figure 9D:
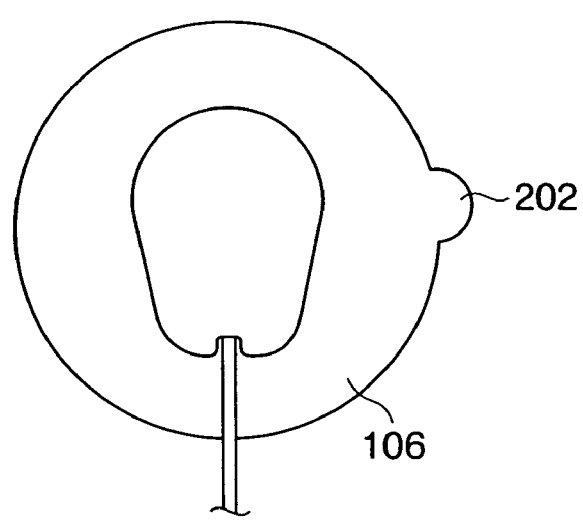

The shape of the waterproof base 106 is described as a perfect circle which is used generally. Alternatively, the base 106 can have other shapes such as an ellipse or oval, as shown in FIG. 9A, or a shape which partly includes a straight line, such as a square, as shown in FIG. 9B. Also, the base 106 can be provided with a corner 201 (FIG. 9C) or a projection 202 (FIG. 9D) to facilitate removal.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A disposable waterproof bioelectrode comprising
a plurality of electrode pads to be attached on a living body and
a plurality of waterproof lead wires respectively connected to said plurality of electrode pads with one-to-one relation, said plurality of waterproof lead wires being formed integrally,
wherein each of said plurality of electrode pads comprises:
a waterproof base member having an adhesive contacting surface and a hole substantially at a center thereof,
a waterproof seal member having a notch substantially corresponding to a sectional shape of one of said plurality of waterproof lead wires in order to prevent water from entering from said one of said plurality of waterproof lead wires, wherein said waterproof seal member fixes said one of said plurality of waterproof lead wires to a back surface of said waterproof base member, wherein said back surface is opposite to said adhesive contacting surface, while covering the hole such that a detection electrode provided to a distal end of said lead wire is exposed through the hole of said waterproof base member, and
a conductive gel arranged on said adhesive contacting surface of said waterproof base member to come into contact with said detection electrode, and
wherein said plurality of waterproof lead wires comprises:
a base film which is common to said plurality of waterproof lead wires and an electrode pattern is provided on one of an upper surface and a lower surface of the base film, and
an upper foam material and a lower foam material each made of a water non-permeable flexible insulating material respectively provided on the upper surface and the lower surface of the base film.

2. The disposable waterproof bioelectrode according to claim 1, wherein ends of said plurality of lead wires which are not to be connected to said electrode pads form a connector.

3. The disposable waterproof bioelectrode according to claim 1, further comprising a first separator to protect said adhesive contacting surfaces of said plurality of electrode pads when said bioelectrode is not in use, wherein said first separator is common to said plurality of electrode pads.

4. The disposable waterproof bioelectrode according to claim 3, wherein
said waterproof base member is made of a flexible film like material, and the waterproof bioelectrode further comprises a second separator provided to a part of said adhesive contacting surface of said waterproof base member, wherein said second separator is provided on at least a part of an outer border of said adhesive contacting surface.

5. The disposable waterproof bioelectrode according to claim 1, wherein at least said waterproof base member of said waterproof base member and said waterproof seal member is formed of a moisture-permeable waterproof film having a thickness of 20 μm to 70 μm.

6. The disposable waterproof bioelectrode according to claim 1, wherein said seal member fixes said lead wire to said waterproof base member from a position inside an outer circumference of said waterproof base member.

* * * * *